United States Patent [19]
Beck et al.

[11] Patent Number: 5,215,527
[45] Date of Patent: Jun. 1, 1993

[54] CATHETER INTRODUCER ASSEMBLY

[75] Inventors: Richard W. Beck, Sandy, Utah; Charles W. Daugherty, Xenia; Steven H. Mersch, Germantown, both of Ohio

[73] Assignee: Becton, Dickinson and Company, Franklin Lakes, N.J.

[21] Appl. No.: 805,780

[22] Filed: Dec. 12, 1991

[51] Int. Cl.$^5$ ............................................. A61M 5/178
[52] U.S. Cl. ..................................... 604/164; 604/43; 604/247; 604/280
[58] Field of Search ..................... 604/9, 43, 158, 164, 604/170, 246, 247, 264, 265, 280

[56] References Cited

U.S. PATENT DOCUMENTS

| | | | |
|---|---|---|---|
| 3,885,561 | 5/1975 | Cami | 604/247 |
| 3,888,249 | 6/1975 | Spencer | 604/247 |
| 4,213,461 | 7/1980 | Pevsner | 604/96 |
| 4,737,152 | 4/1988 | Alches | 604/247 |
| 4,753,640 | 6/1988 | Nichols et al. | 604/247 |
| 4,795,426 | 1/1989 | Jones | 604/164 |
| 4,871,356 | 10/1989 | Haindl et al. | 604/247 |
| 4,955,863 | 9/1990 | Walker et al. | 604/265 |

FOREIGN PATENT DOCUMENTS

3724978 2/1989 Fed. Rep. of Germany ...... 604/247

Primary Examiner—John D. Yasko
Assistant Examiner—Anthony Gutowski
Attorney, Agent, or Firm—Michael G. Schwarz

[57] ABSTRACT

As assembly is provided utilizing a combined catheter and introducer which cooperate to provide efficient infusion of drugs from the in-place assembly even on an intermittent basis with no return blood flow and without the need for any kind of involved valve assembly, or expensive heparin or saline blocks. The introducer is a short thin walled device which receives the catheter therein. The catheter has a plurality of very fine openings in the front end thereof with the openings having a dimension preventing blood backflow, but which allow passage of infusing medication for therapy because of the pressure imparted in the infusion flow of the drugs. The catheter is long enough so that the portion having the openings extends from the front end of the introducer. The front end of the catheter is blunt-ended to decrease trauma during insertion. The openings in the single lumen version extend around the entire circumference of the catheter to prevent the catheter tip from being blocked on one side and closed off. The assembly softens upon exposure to aqueous containing fluids. Moreover, the catheter swells upon insertion to extend to the internal walls of the introducer upon exposure to body fluids. The material of the assembly may include heparin, anti-infective ingredients and lubricants introduced into the polymer material forming the assembly. Finally, the assembly may be multi-lumen for infusing more than one medication through the assembly.

15 Claims, 3 Drawing Sheets

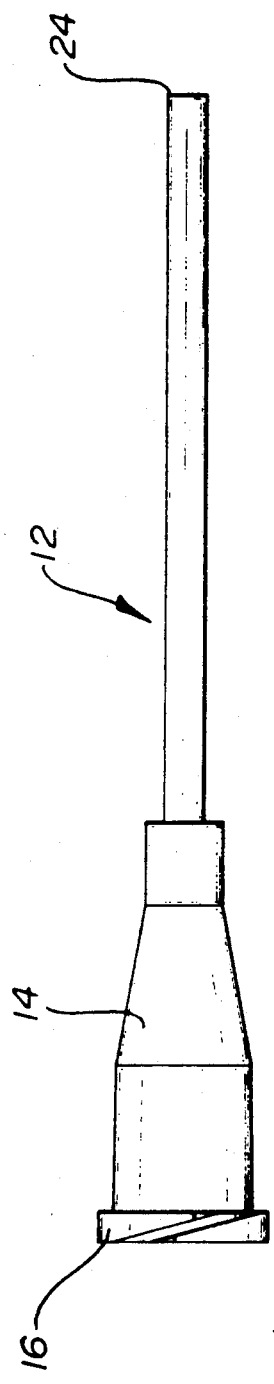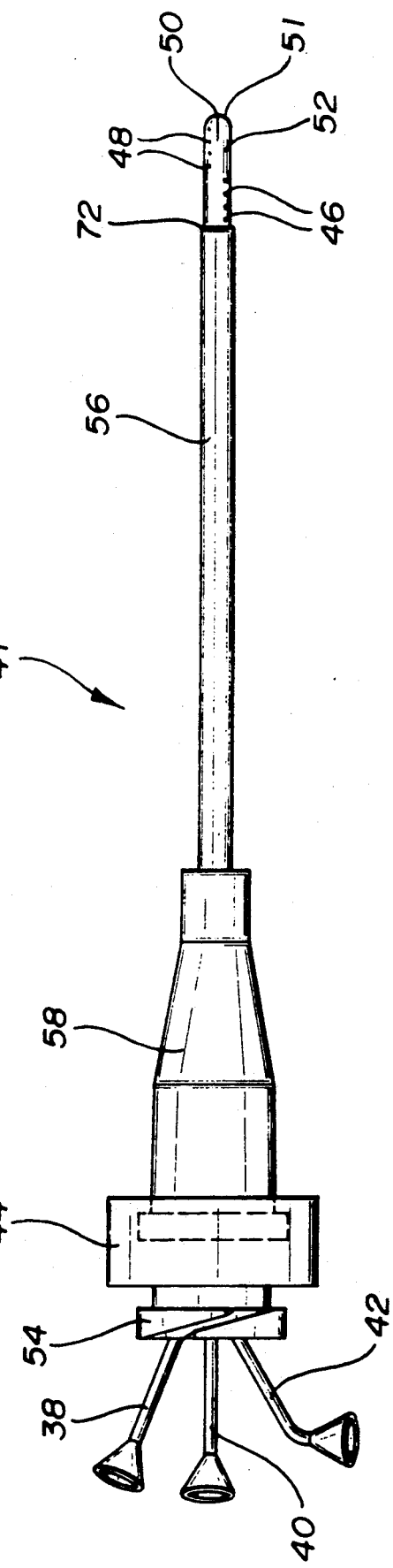

CATHETER INTRODUCER ASSEMBLY

BACKGROUND AND STATEMENT OF THE INVENTION

This invention relates to a catheter introducer assembly for infusing a desired medication into the body of a patient. More particularly, this invention relates to such a catheter intoducer assembly wherein the introducer is a thin-walled but comparatively rigid tubular structure for receiving through the lumen thereof a catheter. The catheter, as a result of the support of the introducer, is of very flexible soft material. Both the catheter and the introducer are comprised of a material, such as a polyurethane, which softens and swells during exposure to body fluids. The material may be hydrophilic. As a result, the assembly, when introduced through the skin of a patient, and when exposed to body fluids, both the introducer and the catheter soften to alleviate any trauma and/or pain to the patient during insertion and subsequent infusion.

More particularly, the introducer is considerably shorter than the catheter so that the front end of the catheter extends outwardly from the front end of the introducer. The catheter includes, in the part which extends from the front end of the introducer, a plurality of openings for infusing liquids into the patient. These openings are of a dimension which allows infusion of liquids under pressure, but which prevents return flow of blood. Therefore, the assembly may be inserted through the skin of a patient and into place for infusion, but liquid infusion may be intermittent without any return blood flow when infusion is not taking place.

The dimensions of the fluid infusion holes through the walls of the front end of the catheter is within the range of between about 0.0005 and 0.005 inches. This allows for discontinuous fluid injection without any return flow. Moreover, the distal or front end of the catheter is rounded to reduce trauma during insertion. Thus, with the combination of the very thin-walled very soft introducer which softens and swells upon exposure to body fluids, and the catheter distal end being comprised of an even thinner-walled material because it is supported by the introducer, and with the front end of the catheter being rounded or having a blunt end, there is a substantial reduction in trauma and/or discomfort to a patient during insertion and during the time when the assembly remains inserted in the patient.

The catheter, moreover, contains an additive so that the infusion holes may be drilled with a laser in a material having sufficient laser absorption characteristics to vaporize under the effect of a laser beam. For more detail involving this procedure, reference is made to U.S. application Ser. No. 350,960, filed, May 11, 1989, which is hereby incorporated by reference in its entirety.

In the past, arrangements have been provided for preventing backflow of body fluids in a catheter assembly. Representative of such structures is taught in U.S. Pat. No. 4,883,461 in which an assembly, with a deliberate return valve, is constructed to prevent backflow. However, the assembly depends upon the movement of the valve and under blood coagulating conditions, this may fail on certain occasions. At any rate, the actual structure described and claimed in U.S. Pat. No. 4,883,461 is arranged to allow body fluid flow for withdrawing body fluids from a patient.

A further patent with an insertion catheter device is that of U.S. Pat. No. 5,009,636 wherein a dual lumen catheter apparatus is provided with multiple openings in the distal end thereof. However, this device is specifically arranged to have openings which receive body fluid for withdrawing from the body as well as inserting body fluid into the body to provide a circulation feature for treating blood and returning it to the body. U.S. Pat. No. 4,976,697 teaches an assembly for allowing insertion of a catheter into the body and allowing placement for intermittent administration of fluids to the patient. In that structure, an obturator assembly is provided for deliberately occluding the catheter when administration is not taking place. The arrangement includes a feed structure for allowing intermittent opening and occlusion of the lumen of the catheter which remains in place.

Finally, U.S. Pat. No. 4,648,519 teaches a plurality of openings in the cap of a container for allowing gas flow through the cap without allowing any liquid flow through the cap. However, this device does not teach or recognize the intermittent introduction of fluids under pressure through orifices of the kind discussed here, while preventing the undesirable flow of blood in the return direction.

With this invention, by contrast, and as noted above, a catheter introducer assembly is provided which utilizes extremely thin-walled structures in the form of an introducer, and a catheter with a blunt nosed distal end, which catheter and introducer both soften upon contact with body fluids for reducing trauma when introduced into the body of a patient for the infusion of fluids. Nevertheless, the assembly, because of its softening nature and thin walls may remain in place without undue trauma to the patient for intermittent infusion of fluids without any return flow of blood or other body fluids from the body through the assembly.

Moreover, because the assembly prevents backflow, expensive heparin and/or saline locks are obviated. The actual polymers comprising the two parts of the assembly herein may have incorporated therein anti-infective ingredients and/or lubricants which have the effect of reducing infection during the in-place positioning of the assembly of the invention, as well as reducing further trauma during insertion.

Other objects and advantages of this invention will be apparent from the following description, the accompanying drawings and the appended claims.

DESCRIPTION OF THE DRAWINGS

FIG. 3 is a longitudinal side elevational view of the introducer portion of the assembly of the invention;

FIG. 4 is a longitudinal side elevational view of a further embodiment of catheter introducer assembly of the invention illustrating a multi-lumen catheter in the assembly;

DETAILED DESCRIPTION OF THE INVENTION

Figure 1:
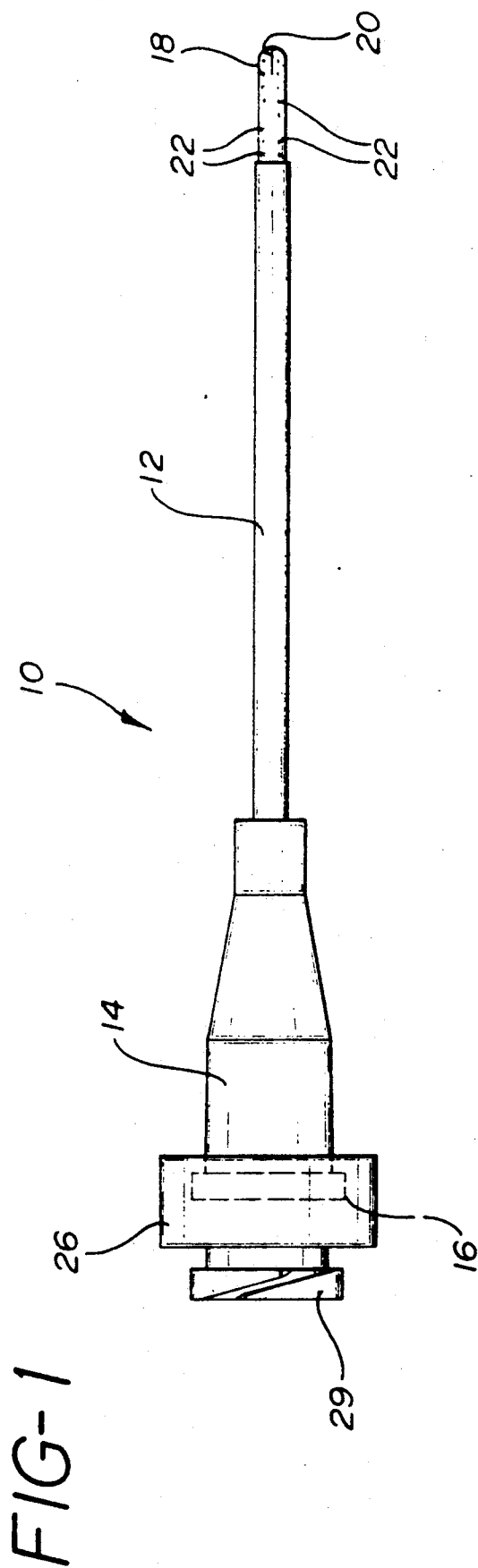
FIG. 1 is a longitudinal side elevational view illustrating one embodiment of the catheter introducer assembly of the invention.
Figure 2:
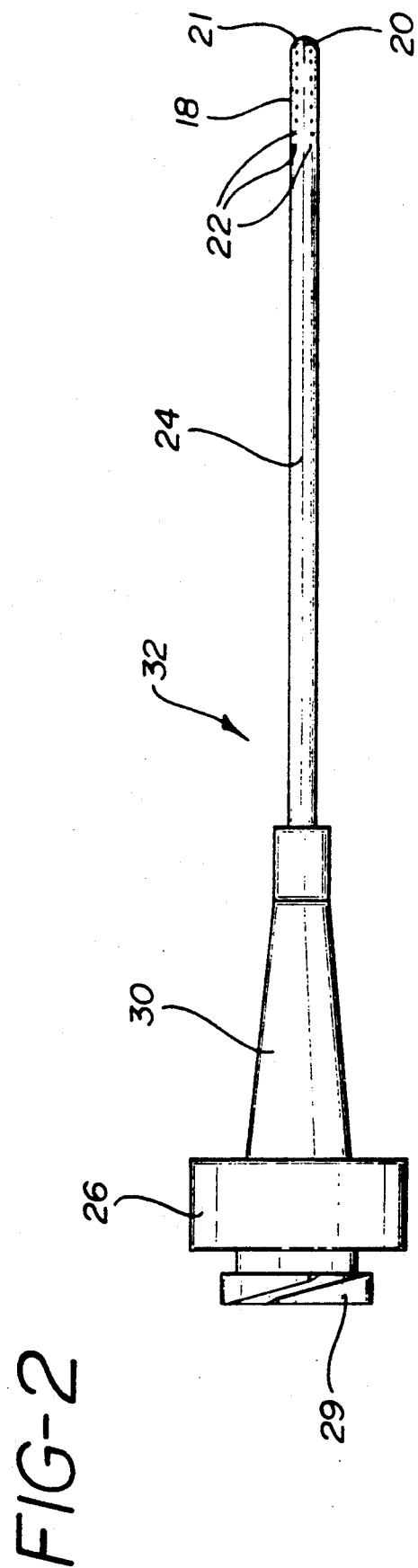
FIG. 2 is a longitudinal side elevational view of the catheter portion of the catheter introducer assembly of the invention and illustrating one form of outlet configuration of the invention for the infusion of body fluids.

Referring to the drawings in which like reference characters refer to like parts throughout the several views thereof, FIG. 1 illustrates the invention as employed in a catheter introducer assembly 10 having an introducer portion 12 extending from a main body 14. Body 14 has a connection 16 on the proximal end thereof for receiving the connection 26 of the catheter 32 (FIG. 2). Catheter 32 extends from a main body or luer connector 30 which is connected to connection 26, as shown in FIG. 2. The catheter 32 has on the proximal end thereof an opening assembly 29 for receiving a connection for a supply of medication for infusion into a patient.

Catheter 32 includes an elongated very thin walled fluid passage portion 24 which encompasses the lumen of the catheter, and extends to and feeds the very small openings 22 in the front distal end 18 of catheter 32. As can be seen in FIG. 2, this particular embodiment includes, in addition to openings 22, a one way slit valve 20. Moreover, the front end 21 of catheter 32, as can be seen in FIG. 2, is blunt ended, or ball nosed, to reduce trauma during insertion.

It is within the purview of this invention that the elongated front end 24 of catheter 32 is of an extremely soft thin wall and the wall is comprised of a soft material, because of the fact that the introducer portion of the assembly is of a stiffer supporting material. At any rate, both the introducer and the catheter portion of the assembly may be comprised of Vialon ® a polyurethane material manufactured by Becton, Dickinson and Company, Franklin Lakes, N.J. 07417-1880. Vialon ® was particularly developed as a material which softens rapidly upon exposure to aqueous containing fluids such as blood or other body fluids.

Moreover, it is within the purview of this invention that the introducer walls themselves may be very thin and approximately 0.002 inches, and perhaps as thin as 0.001 inches in thickness. While the wall of the introducer is comprised of a polymer which is stiffer for supporting the very soft flexible catheter, it is still of a thin material which softens rapidly upon insertion into the patient. In each case, the Vialon ® is modified to have the desired characteristics, as discussed above.

Referring now to FIG. 4, a further embodiment of the invention is illustrated in the form of a multi-lumen catheter assembly 41 having an introducer 56 with a connection head 58 on the rear end thereof for receiving the connection head 44 of the related catheter 52 portion of the assembly 41. As can be seen in FIG. 4, the assembly 41 includes three separate luer connections 38, 40 and 42 for introducing separate selected medications and/or other fluids into the separate lumens of the multi-lumen assembly of the catheter 52 illustrated in FIG. 5. These connections 38, 40 and 42 feed to the rear connection 54 of catheter 52.

Figure 5:
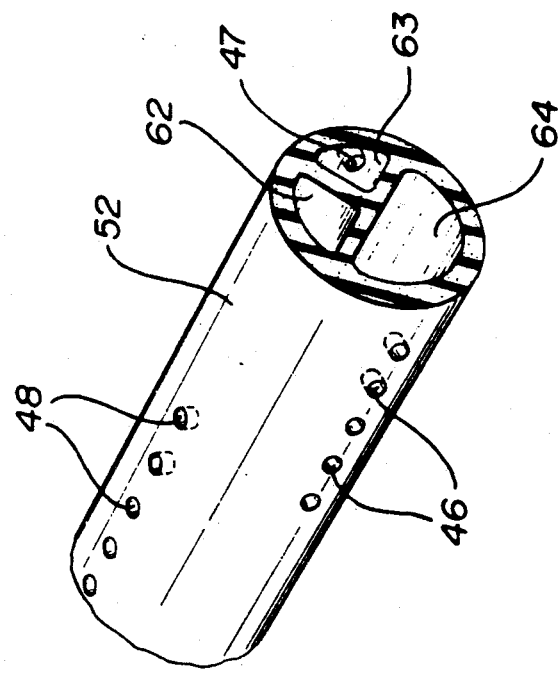
FIG. 5 is a perspective view partially in section of the catheter portion of the assembly of FIG. 4, and showing the positioning of the lumens relatively to the ports or holes for the lumens.

As can be seen in FIG. 4, the catheter 52 extends forwardly from the front distal end 72 of the introducer portion 56 of the assembly 41. Moreover, it also has a blunt end 51 for ease of insertion into a patient. Catheter assembly 41 includes a catheter having a plurality of openings 46 which are fed by one lumen 64, as will be described below. A separate group of openings 48 are fed by an additional lumen 62. It should be understood that more than three lumens may be utilized with each lumen having its own individual set of holes. Moreover, even though each set of holes is in a straight line, as shown in FIG. 5, they may be positioned in a zig-zag arrangement, for example. Finally, slit valve 50 is fed by an additional lumen 72, as shown in the sectional view of FIG. 6.

Figure 6:
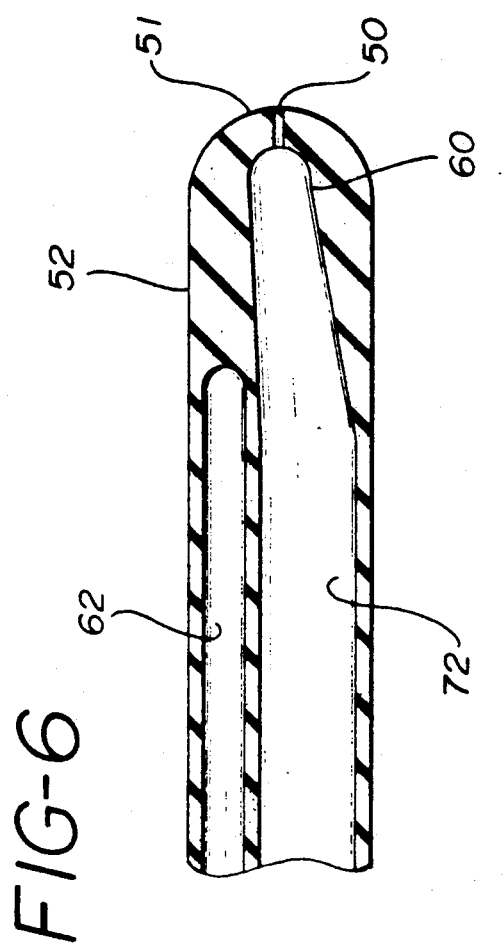
FIG. 6 is a cross sectional view of the catheter of FIG. 4 illustrating the positioning of one lumen feeding to the split blunt nose.

That is, and referring to FIG. 6 showing a cross section of the catheter 52, lumen 72 feeds to slit valve 50.

Figure 7:
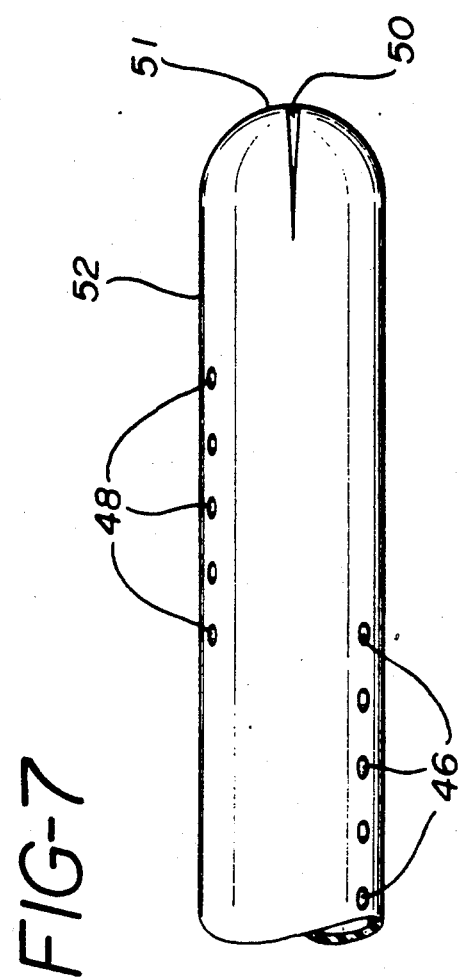
FIG. 7 is a partial side elevational view of the distal end of the catheter of FIG. 4 and illustrating the split blunt nose of the invention.

As can be seen in FIG. 7, openings 48 are in one circumferential position in the walls of catheter 52 and openings 46 are in a separate circumferential position. Lumen 72 passes throuqh this area to feed the slit valve 50 in the distal end of catheter 52.

In this connection, it should be understood that one of the features of the invention is the fact that the openings such as 22 in the single lumen version 32 of the catheter of the invention extend around the entire circumference of the related catheter so as to preclude blockage of fluid when infusion is desired. That is, one portion of the circumferential extent of the distal end of the catheter may be blocked or otherwise obstructed. Because holes are around the entire circumferential extent, infusion may still take place.

As a further feature of this invention, and as discussed above, the two parts forming the assembly of the invention in the form of an introducer and a catheter are comprised of Vialon ® which swells when exposed to body fluids or aqueous containing fluids of any kind. Because of this, the catheter swells adjacent the front end of the assembly of the invention so that the outer diameter of the walls thereof engage the inner diameter of the walls of the lumen of the introducer portion of the assembly. This has the effect of sealing the two parts, once introduced through the skin of a patient, for preventing any body fluids from passing in between the outer walls of the catheter of the assembly and the inner walls of the introducer portion of the assembly.

Thus, as will be appreciated by practitioners-in-the-art, an extremely soft gentle assembly is provided for insertion throuqh the skin of a patient for infusing medication to that patient with a substantially reduced trauma to the patient during this procedure. Moreover, the assembly provides, without any involved valving structure, for intermittent infusion of liquids and stopping of that infusion as required for proper medication introduction into a patient over time.

Because of the extremely soft nature of the assembly and the fact that it softens further when introduced and exposed to body fluids, the fact that the assembly may remain in place for a period of time for intermittent feeding of medication makes the assembly particularly desirable for patients. And as discussed above, because the material forming the assembly of the invention may be formulated to include heparin, anti-infective ingredients, and lubricants, the configuration of the assembly of the invention is enhanced to prevent coagulation, infection and to ease insertion even further when the assembly is placed.

While the forms of apparatus herein described constitute preferred embodiments of this invention, it is to be understood that the invention is not limited to these precise forms of apparatus, and that changes may be made therein without departing from the scope of the invention which is defined in the appended claims.

What is claimed is:

1. A catheter introducer assembly comprising
   (a) an elongated catheter body;
   (b) said elongated catheter body having a first end and a second end;
   (c) means at said first end for receiving medication for infusion into a patient;
   (d) a plurality of substantially round holes positioned around the circumference of said catheter adjacent said second end of said catheter;
   (e) a lumen extending through said catheter body from said medication receiving end to said holes;
   (f) said holes being dimensioned to prevent blood flow therethrough into said lumen but to allow medication to flow out of said lumen;
   (g) an elongated catheter introducer for assisting the introduction of said catheter second end through the skin of a patient;
   (h) said catheter introducer having very thin walls and a first end adjacent said catheter first end and a second end adjacent said catheter second end; with said very thin walls extending from said first end to said second end;
   (i) a lumen in said introducer extending from the said first end thereof to said second end for receiving said catheter therethrough; and
   (j) said introducer being shorter than said catheter so that the said second end of said catheter and said plurality of holes extend outwardly from said second end of said introducer.

2. The assembly of claim 1, wherein
   (a) said catheter second end is rounded to present a blunt end when inserted into the skin of a patient.

3. The assembly of claim 2, wherein
   (a) a one-way slit valve is positioned in said rounded second end.

4. The assembly of claim 1, wherein
   (a) said holes have diameters within a range of between about 0.0005 and 0.005 inches.

5. The assembly of claim 1, wherein
   (a) said very thin walls of said introducer are within the range of between about 0.001 and 0.002 inches thick.

6. The assembly of claim 1, wherein
   (a) said catheter and said introducer are comprised of a material which swells upon contact with aqueous containing body fluids.

7. A catheter introducer assembly wherein said catheter has a plurality of lumens for introducing more than one medication into a patient, said assembly comprising
   (a) an elongated catheter body;
   (b) said elongated catheter body having a first end and a second end;
   (c) a plurality of lumens extending through said catheter body from said first end to said second end;
   (d) a medication receiving connection connected to each of said plurality of lumens at said first end of said catheter body;
   (e) a plurality of substantially round holes positioned in the walls of said catheter body adjacent said second end;
   (f) said plurality of holes being positioned so that a portion thereof is separately connected to each of said plurality of lumens;
   (g) said holes being dimensioned to prevent blood flow therethrough into their respective lumens but to allow medication to flow out of said respective lumen;
   (h) an elongated catheter introducer for assisting the introduction of said catheter second end through the skin of a patient;
   (i) said catheter introducer having very thin walls and a first end adjacent said catheter first end and a second end adjacent said catheter second end, with said very thin walls extending from said introducer first end to said introducer second end;
   (j) a lumen in said introducer extending from the said first end thereof to said second end for receiving said catheter therethrough; and
   (k) said introducer being shorter than said catheter so that the said second end of said catheter and said plurality of holes extend outwardly from said second end of said introducer.

8. The assembly of claim 7, wherein
   (a) said catheter second end is rounded to present a blunt end when inserted into the skin of a patient.

9. The assembly of claim 8, wherein
   (a) a one-way slit valve is positioned in said rounded second end, said one way slit valve connected to one of said plurality of lumens.

10. The assembly of claim 7, wherein
    (a) said plurality of holes have a diameter within the range of between about 0.0005 and 0.005 inches.

11. The assembly of claim 7, wherein
    (a) said very thin walls of said introducer are within the range of between about 0.001 and 0.002 inches thick.

12. The assembly of claim 7, wherein
    (a) said catheter and said introducer are comprised of a material which swells upon contact with aqueous containing body fluids.

13. A catheter introducer assembly comprising
    (a) an elongated catheter body;
    (b) said elongated catheter body having a first end and a second end;
    (c) means at said first end for receiving medication for infusion into a patient;
    (d) a plurality of holes positioned around the circumference of said catheter adjacent said second end of said catheter said holes having diameters within the range of between about 0.0005 and 0.005 inches;
    (e) a lumen extending through said catheter body from said medication receiving end to said holes;
    (f) said holes being dimensioned to prevent blood flow therethrough into said lumen but to allow medication to flow out of said lumen;
    (g) an elongated catheter introducer for assisting the introduction of said catheter second end through the skin of a patient;
    (h) said catheter introducer having very thin walls and a first end adjacent said catheter first end and a second end adjacent said catheter second end; with said very thin walls extending from said first end to said second end;
    (i) a lumen in said introducer extending from the said first end thereof to said second end for receiving said catheter therethrough; and
    (j) said introducer being shorter than said catheter so that the said second end of said catheter and said plurality of holes extend outwardly from said second end of said introducer.

14. A catheter introducer assembly wherein said catheter has a plurality of lumens for introducing more than one medication into a patient, said assembly comprising
    (a) an elongated catheter body;
    (b) said elongated catheter body having a first end and a second end;
    (c) a plurality of lumens extending through said catheter body from said first end to said second end;
    (d) a medication receiving connection connected to each of said plurality of lumens at said first end of said catheter body;
    (e) a plurality of substantially round holes positioned in the walls of said catheter body adjacent said second end;
    (f) said plurality of holes being positioned so that a portion thereof is separately connected to each of said plurality of lumens;
    (g) said holes being dimensioned to prevent blood flow therethrough into their respective lumens but to allow medication to flow out of said respective lumen;
    (h) an elongated catheter introducer for assisting the introduction of said catheter second end through the skin of a patient;
    (i) said catheter introducer having very thin walls and a first end adjacent said catheter first end and a second end adjacent said catheter second end, with said very thin walls extending from said introducer first end to said introducer second end;
    (j) a lumen in said introducer extending from the said first end thereof to said second end for receiving said catheter therethrough; and
    (k) said introducer being shorter than said catheter so that the said second end of said catheter and said plurality of holes extend outwardly from said second end of said introducer.

15. The assembly of claim 14, wherein
    (a) said holes have diameters within the range of between about 0.0005 and 0.005 inches.

* * * * *